United States Patent [19]

Altes et al.

[11] Patent Number: 5,357,025

[45] Date of Patent: Oct. 18, 1994

[54] SEALANT WITH SILOXAPHOBIC SURFACE, COMPOSITION, AND METHOD TO PREPARE SAME

[75] Inventors: Michael G. Altes; Louise C. Bergman, both of Midland; Nedeljko V. Gvozdic; Jerome M. Klosowski, both of Bay City; Virginia K. O'Neil, Midland, all of Mich.

[73] Assignee: Dow Corning Corporation, Midland, Mich.

[21] Appl. No.: 136,507

[22] Filed: Oct. 14, 1993

Related U.S. Application Data

[62] Division of Ser. No. 935,495, Aug. 25, 1992.

[51] Int. Cl.$^5$ ............................................. C08G 77/24
[52] U.S. Cl. ............................ 528/42; 556/428; 556/422; 556/470; 528/34
[58] Field of Search ............................................ 528/42

[56] References Cited

U.S. PATENT DOCUMENTS

| | | | |
|---|---|---|---|
| 2,993,925 | 7/1961 | Husted | 528/42 |
| 3,828,087 | 8/1974 | Pittman | 528/42 |
| 4,460,740 | 7/1984 | Arai | 524/724 |
| 4,683,251 | 7/1987 | Mikami | 522/46 |
| 4,695,603 | 9/1987 | Inoue et al. | 524/723 |
| 5,126,420 | 6/1992 | Satoh et al. | 528/32 |
| 5,235,017 | 8/1993 | O'Lenick, Jr. | 528/26 |

OTHER PUBLICATIONS

Noll, Chemistry and Technology of Silicones, 1968, pp. 142–147.

*Primary Examiner*—John C. Bleutge
*Assistant Examiner*—Margaret W. Glass
*Attorney, Agent, or Firm*—Roger H. Borrousch

[57] ABSTRACT

A sealant made from a room temperature curing polydimethylsiloxane composition has a siloxaphobic surface layer at the air-sealant interface where this layer is a fluorocarbon compound and a drying oil oxidation product. Elastomeric compositions made from polydimethylsiloxanes having both low reactivity endgroups and high reactivity endgroups and a siloxaphobic agent of fluorocarbon alcohol or a reaction product of the fluorocarbon alcohol and a hydrolyzable silane, are particularly useful for sealing buildings because they can withstand the expansions and contractions. One siloxaphobic agent is the reaction product between a fluorocarbon alcohol and a methyltri(methylethylketoximo)silane and the formula of one of the reaction product compounds is

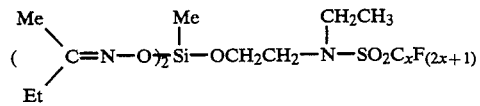

wherein x has an average value of at least 6.

15 Claims, No Drawings

SEALANT WITH SILOXAPHOBIC SURFACE, COMPOSITION, AND METHOD TO PREPARE SAME

This is a divisional of copending application 07/935,495 filed on Aug. 25, 1992, pending.

BACKGROUND OF THE INVENTION

1. Field of the Invention

This invention relates to non-staining room temperature vulcanizable silicone sealants, compositions, and methods to prepare same.

2. Prior Art

Many methods have been proposed to eliminate the problem encountered with the use of room temperature curing silicone sealants in construction of buildings of becoming dirty and of staining the surrounding building materials adjacent to the sealant. This creates an unattractive appearance. Cleaning the dirt off of the sealant and the stain off the adjacent building materials is an expensive method and the results are often unsatisfactory. It is therefore the hope of the construction industry that a silicone sealant be developed which does not itself become dirty or stain the adjacent building materials.

The staining of building materials adjacent to the sealant apparently occurs when materials, such as polyorganosiloxanes migrate to these surfaces from the cured sealant and contaminants from the air or precipitation adhere to these surfaces and they become stained. The aesthetics of the building are reduced. The construction industry is therefore interested in sealants which overcome this problem. Certain surfactants have been proposed to overcome this drawback of the room temperature silicone sealants. Some of these surfactants include the nonionic or anionic surfactants containing polyoxyethylene segment, sorbitan, or disaccharide residual groups in the polyoxyethylene described in an abstract for Japanese Kokai [Laid Open] Patent Publication No. 56-76453 [81-76453], assigned to Toshiba Silicone KK, Jun. 24, 1981; and an abstract for Japanese Kohai [Laid Open] Patent Publication No. 56-76452 [81-76452], assigned to Toshiba Silicone KK, Jun. 24, 1981. These surfactants appear to be effective to reduce the surface dirt pick up but only when large amounts are used. The use of large amounts of these surfactants leads to a decrease in adhesion of sealant to building materials and this is unsatisfactory.

Another solution to the sealant becoming dirty and the surfaces adjacent to the sealant staining, was proposed by Arai in U.S. Pat. No. 4,460,740, issued Jul. 17, 1984. Arai teaches that conventional silicone sealant compositions which contain a limited amount of a specific fluorine-containing surface active agent solves the problem, encountered by cured sealant when used for sealing or caulking of a joint in building structures, of surface staining which eventually spreads over adjacent surfaces. Arai teaches that the fluorine-containing surface active agents can be amphoteric, anionic, cationic, and non-ionic surface active agents. Arai illustrates the amphoteric fluorine-containing surface active agents by the following formulae

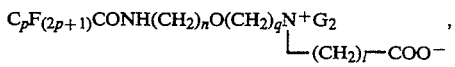

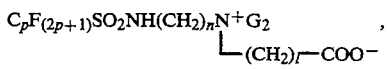

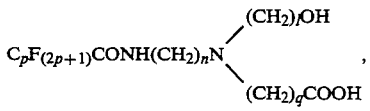

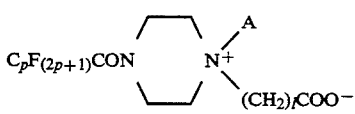

in which G is a monovalent organic group or preferably, a monovalent hydrocarbon group, A is an alkyl group or a hydroxyalkyl group, l, n, and q are each zero or a positive integer and p is a positive integer. Anionic surface active agents are described as $C_pF_{(2p+1)}SO_3M$ or $C_pF_{(2p+1)}COOM$, in which M is a hydrogen atom or an alkali metal atom. Cationic surface active agents are illustrated by the formula $C_pF_{(2p+1)}SO_2NH(CH_2)_nN^+G_3W^-$ in which W is a halogen atom and R, n, p are defined above. The nonionic surface active agents are illustrated by the formula $C_pF_{(2p+1)}SO_2NG(CH_2CH_2O)_uH$ in which u is zero or a positive integer and G and p are described above.

Arai teaches that these particular fluorine-containing surface agents are useful in a silicone sealant composition of from 0.01 to 5.0 parts by weight per 100 parts by weight of the total components where the composition is 100 parts by weight of a diorganopolysiloxane blocked on both molecular chain ends with a hydroxy group directly bonded to silicon atom, 0.1 to 25 parts by weight of an organosilicon compound having at least two hydrolyzable groups per molecule on the average, 1 to 400 parts by weight of a filler, and optionally up to 5.0 parts by weight of a curing catalyst. Such compositions are taught as insusceptible to stain on the surface of a cured rubbery elastomer. Arai teaches that these compositions cure to sealants which begin to show surface stain after outdoors exposure from 1 to 6 months depending upon the particular fluorine-containing surface active agent used. The fluorine-containing surface active agents showing the best results were the amphoteric surface active agents.

Arai, along with Yoshio Inoue and Takeo Inoue (Inoue et al), in U.S. Pat. No. 4,695,603, issued Sep. 22, 1987, teach that long term resistance to stain is not accomplished by sealant compositions containing the fluorine-containing surface active agent as described by Arai in U.S. Pat. No. 4,460,740. Inoue et al teach that in order to obtain surface stain resistance, in addition to the fluorine-containing surface active agent, an organosilicon compound of the following formula is required

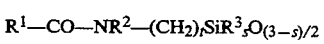

in which $R^1$, $R^2$, and $R^3$ are each a hydrogen atom, a monovalent hydrocarbon group, or a monovalent hydrocarbon group substituted with halogen or cyano, s is zero, 1, 2, or 3, and t is a positive integer not larger than 10. These organosilicon compounds are present in the composition in amounts of from 0.01 to 10 parts by weight. The use of both of the fluorine-containing surface active agent of Arai and the organosilicon compound of Inoue et al show that the onset of stain may begin after 12 months depending upon the particular fluroine-containing surface active agents, the particular organosilicon compound, and their amounts in the sealant composition.

Although the prevention of surface staining and staining of adjacent surfaces of up to 12 months is an advantage, buildings are intended to last for many years and the prevention of sealant surface staining and dirtying and/or staining on building materials adjacent to the cured sealant is desirable for as long as possible. Therefore, an extensive development program was initiated to provide sealants which would maintain clean surfaces on the sealant and which would maintain adjacent building material surfaces clean over years of exposure to atmospheric conditions.

SUMMARY OF THE INVENTION

This invention relates to a polyorganosiloxane elastomeric sealant comprising a room temperature cured polyorganosiloxane composition having an interface with air where a siloxaphobic surface layer covers the air interface in which the siloxaphobic surface layer comprises a fluorocarbon compound which contains per molecule at least one fluorocarbon group of the formula $C_xF_{(2x+1)}$— where x has an average value of at least 6 and a drying oil oxidation product.

Another embodiment of this invention is an polyorganosiloxane composition which cures at room temperature to an elastomer but remains uncured when protected from moisture comprising (A) a polydimethylsiloxane comprising a mixture of different molecular species which together have a viscosity at 25° C. of from 3 to 400 Pa.s and which together have low reactivity endgroups in an amount to provide from $>0$ to $\leqq 30\%$ of the total number of endgroups wherein the low reactivity endgroups have a formula $$X_aR_{(3-a)}SiO-$$

wherein a is 0 or 1, R is a monovalent hydrocarbon radical, and X is R, HO—, or a hydrolyzable group containing at least one carbon atom, and have high reactivity endgroups in an amount of from $\geqq 70$ to $<100\%$ of the total number of endgroups wherein the high reactivity endgroups have a formula $$Y_bR_{(3-b)}SiO-$$

or $$Y_bR_{(3-b)}SiCH_2CH_2-$$

wherein b is 2 or 3, R is a monovalent hydrocarbon radical, and Y is a hydrolyzable group containing at least one carbon atom, (B) a hydrolyzable silane of an average general formula $$R_{(4-c)}SiY_c$$

wherein R is a monovalent hydrocarbon radical, c has an average value of from 2 to 4 inclusive and Y is a hydrolyzable group, where the amount of hydrolyzable silane present in the composition is in an amount of at least 0.5 weight percent based on the total weight of the composition, (C) a siloxaphobic agent selected from the group consisting of a fluorocarbon alcohol, a reaction product of a fluorocarbon alcohol and a hydrolyzable silane as defined in (B), and a mixture thereof, wherein the fluorocarbon alcohol contains at least one fluorocarbon group of the formula $C_xF_{(2x+1)}$— where x has an average value of at least 6, the fluorocarbon group being present in an amount of from 0.1 to 7 inclusive weight percent based on the weight of the composition, and (D) a filler.

A further embodiment of this invention is a method comprising, under conditions to exclude moisture from contacting ingredients, (1) mixing a fluorocarbon alcohol containing per molecule at least one fluorocarbon group of the formula $C_xF_{(2x+1)}$— in which x has an average value of at least 6 and a hydrolyzable silane of an average general formula $$R_{(4-c)}SiY_c$$

wherein R is a monovalent hydrocarbon radical, c has an average value of from 2 to 4 inclusive and Y is a hydrolyzable group, to make a mixture where there is at least 0.01 mole of fluorocarbon alcohol per one mole of hydrolyzable silane molecule, (2) heating the mixture of (1) until some of the fluorocarbon alcohol reacts with the hydrolyzable silane wherein a C—O—Si bond is formed and a reaction mixture of the hydrolyzable silane and the fluorocarbon alcohol results and comprises, unreacted fluorocarbon alcohol, unreacted hydrolyzable silane, and a reaction product of the hydrolyzable silane and the fluorocarbon alcohol, and (3) mixing the reaction product of (2) with a room temperature curing elastomeric polyorganosiloxane composition in an amount such that there is from 0.1 to 7 weight percent of the fluorocarbon group based on the total weight of the composition to make a room temperature curing sealant which produces a siloxaphobic surface when cured by exposure to atmospheric conditions.

Another embodiment of this invention is a method for making a siloxaphobic agent comprising, under conditions to exclude moisture from contacting ingredients, (1) mixing a fluorocarbon alcohol containing per molecule at least one fluorocarbon group of the formula $C_xF_{(2x+1)}$— in which x has an average value of at least 6 and a hydrolyzable silane of an average general formula $$R_{(4-c)}SiY_c$$

wherein R is a monovalent hydrocarbon radical, c has an average value of from 2 to 4 inclusive and Y is a hydrolyzable group, to make a mixture where there is at least 0.01 mole of fluorocarbon alcohol per one of hydrolyzable silane molecule, (2) heating the mixture of (1) until some of the fluorocarbon alcohol reacts with the hydrolyzable silane wherein a C—O—Si bond is formed and a reaction mixture of the hydrolyzable silane and fluorocarbon alcohol results and comprises, unreacted fluorocarbon alcohol, and unreacted hydrolyzable silane, and a reaction product of the hydrolyzable silane and the fluorocarbon alcohol.

DESCRIPTION OF THE PREFERRED EMBODIMENTS

Polyorganosiloxane elastomeric sealants of this invention have a siloxaphobic surface layer at the interface between air and the cured sealant. A siloxaphobic surface layer is both siloxaphobic and hydrophilic and is a relatively thin layer at the air-sealant interface which hinders the migration of siloxane species which are unreacted into the cured sealant matrix and migrate out of the sealant matrix to the air-sealant interface. The siloxaphobic surface layer does not readily allow siloxanes to penetrate out of the sealant matrix onto the sealant surface and onto adjacent substrates, such as building materials. A siloxaphobic surface layer also hinders the formation of dirt build-up or staining of the surface of the cured sealant. Additionally, a siloxaphobic surface layer can be one to which paint will adhere.

The polyorganosiloxane elastomeric sealants of this invention are obtained by curing room temperature vulcanizable polyorganosiloxane compositions which produce a siloxaphobic surface layer. A fluorocarbon compound which contains at least one perfluoralkyl group having at least six carbon atoms and a drying oil in a room temperature vulcanizable polyorganosiloxane composition produces, when the composition is cured, a siloxaphobic surface layer at the air-sealant interface which comprises the fluorocarbon compound and a drying oil oxidation product. The drying oil oxidation product enhances the siloxaphobic properties of the siloxaphobic surface layer and also provides a surface which can be painted with either oil based paints or latex based paints. The preferred fluorocarbon compounds are fluorocarbon alcohols or fluorocarbon alcohol derivatives.

The drying oils can be an ester compound derived from unsaturated fatty acids having at least ten carbon atoms and alcohols. The unsaturated fatty acids include oleic, linoleic, linolenic, eleostearic, licanic, ricinoleic, and arachidonic acids. The ester compounds include mixtures which preferably contain at least 80 weight percent of the ester compounds made from unsaturated fatty acids having at least 10 carbon atoms. Many of the unsaturated fatty acid esters can be found in natural drying oils obtained from plant and animal sources, such as illustrated by linseed oil, tung oil, soybean oil, caster oil, fish oil, hempseed oil, cottonseed oil, oiticica oil, and rapeseed oil. The drying oil oxidation product is the material obtained when a drying oil reacts (polymerizes) through reaction with oxygen, such as air.

A preferred polyorganosiloxane elastomeric sealant is one in which the siloxaphobic surface layer comprises a fluorocarbon alcohol and the drying oil oxidation product is tung oil oxidation product.

Polyorganosiloxane elastomeric sealants which have, after 7 days exposure to an air atmosphere of 50% relative humidity at 25° C. an elongation at break of greater than 500%, a tensile strength at break of greater than 600 kPa (kilo-Pascals), and a modulus at 100% elongation of less than 800 kPa where these values are measured by ASTM D-412 procedure are preferred. These sealants also have less than 15% extractable materials using the procedure of ASTM D 3971-69 in which toluene was used as the solvent, the time period was 24 hours, and the sealant was cut into pieces of 3.175 mm (millimeters) by 3.175 mm by 2.54 mm. Polyorganosiloxane elastomeric sealant compositions which cure to give sealants with these properties and the siloxaphobic surface layer are preferred. They provide the unique long term clean sealant surface and equally long term clean substrates adjacent to the cured sealant. At the same time, they maintain these properties making them advantageous to form seals where expansions and contractions occur from heating and cooling of substrates, such as in buildings. The elastomeric polydimethylsiloxane compositions of this invention can be packaged in one or two packages. Such packaging is well known in the art.

It is believed that the siloxaphobic surface layer is a closely packed surface layer at the air-sealant interface and this layer has a significantly low dispersive force contributing to the surface energy and the unreacted silicone species do not easily migrate through or across this surface layer. The siloxaphobic surface layers have surface energies which have a dispersive force component and a polar force component where the dispersive force component is less than or equal to 15 dynes/cm$^2$ and the polar force component is greater than 0 dynes/cm$^2$. The siloxaphobic surface layer forms at the air-sealant interface and does not appear to form at the substrate-sealant interface, such as the interface between the sealant and substrates such as glass, aluminum, concrete, and the like. The silxoaphobic surface interface is thus unique in that the adhesion of the sealant to the substrate is not substantially changed.

The polyorganosiloxane compositions which cure to elastomers at room temperature when exposed to moisture, but remain uncured when protected from moisture are made from (A) polydimethylsiloxanes having both low reactivity endgroups and high reactivity endgroups, (B) a hydrolyzable silane, (C) a siloxaphobic agent which is a fluorocarbon alcohol or which is a mixture of a fluorocarbon alcohol and a reaction product of the fluorocarbon alcohol and the hydrolyzable silane, and (D) a filler.

Polydimethylsiloxane (A) comprises a mixture of different molecular species. The viscosity of (A) can be from 3 to 400 Pa.s (Pascal-seconds), preferably from 50 to 100 Pa.s. The polydimethylsiloxane (A) is preferably a mixture of molecular species which together has $>0\%$ to $\leq 30\%$ of the endgroups being low reactivity and $\geq 70\%$ to $<100\%$ of the endgroups being high reactivity. In this mixture, some molecules can have both endgroups as either low reactivity or high reactivity, and some molecules can have one endgroup low reactivity and the other endgroup high reactivity, but the average of the mixture will fall in the range as stated above. These mixtures of (A) can be made prior to combining with the other ingredients or they can be made in situ. The preferred polydimethylsiloxane (A) are those which have from 5% to 20% of the endgroups being low reactivity and from 80% to 95% of the endgroups being high reactivity. These preferred polydimethylsiloxanes provide a low modulus sealant which is desirable for sealant joints in building constructions.

The low reactivity endgroups have the following formula

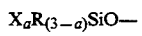

in which a is 0 or 1, R is a monovalent hydrocarbon radical, and X is R, HO—, or a hydrolyzable group containing at least one carbon atom. The high reactivity endgroups have the following formula $Y_bR_{(3-b)}SiO-$ or $Y_bR_{(3-b)}SiCH_2CH_2-$ in which b is 2 or 3, R is a monovalent hydrocarbon radical, and Y is a hydrolyzable group containing at least one carbon atom.

Polydimethylsiloxane (A) can be made by various methods. For example, a mixture of a polydimethylsiloxane in which both endgroups are hydroxyl groups and a polydimethylsiloxane in which both endgroups are triorganosilyl groups, such as trimethylsilyl wherein the mixture has an average of >0% to ≦30% of the endgroups as triorganosilyl groups (low reactivity endgroups) and ≧70% to <100% of the endgroups as hydroxyl groups (high reactivity endgroups). The higher the percentage of the endgroups which are low reactivity the lower the modulus of the resulting cured sealant, given that the other ingredients remain relatively constant in the sealant composition.

A method of making the polydimethylsiloxanes of (A) is illustrated by the method described by Dupree in U.S. Pat. No. 3,274,145, issued Sep. 20, 1966. Dupree describes the preparation of polydimethylsiloxanes in which the terminal radicals are in part siloxanols and in part triorganosilyl groups. Dupree describes four method of making these polydimethylsiloxanes. In his first method, a calculated amount hexaorganodisiloxane or a low molecular weight triorganosilyl endblocked polydimethylsiloxane is polymerized with cyclic polydimethylsiloxane or hydroxyl endblocked polydimethylsiloxane or both in the presence of a bond-rearranging catalyst such as potassium hydroxide. A second method of Dupree is combining a mixture of hydroxyl endblocked polydimethylsiloxane with a triorganosilanol or triorganosilyldisiloxanol with a condensation catalyst. A third method of Dupree reacts a triorganohalosilane with a hydroxyl endblocked polydimethylsiloxane in the presence of an acid acceptor, such as alpha-picoline. Although a fourth method is described by Dupree, it would first involve forming polymer using one of the other methods. Dupree is hereby incorporated by reference to show methods for preparing polydimethylsiloxane of (A) in which some endgroups are low reactivity, such as trimethylsilyl groups and other endgroups are high reactivity, such as the hydroxyl groups bonded to the silicon atoms of the terminals. Dupree teaches that increasing the number of endgroups which are triorganosiloxy groups decreases the modulus.

Another polydimethylsiloxane (A) can be made by reacting polydimethylsiloxane which has hydroxyl groups at both ends with a silane having at least three hydrolyzable groups per molecule and has the formula $R_{(4-c)}SiY_c$  Formula A in which c is 3 or 4, preferably c is 3, Y is ketoximo and methoxy, and R is methyl. The amount of silane of Formula A is that amount sufficient to react with less than the hydroxyl groups of the polydimethylsiloxane. For highly reactive silanes, this amount can be less than one silane molecule per hydroxyl group of the polydimethylsiloxane. For silanes having lower reactivity, the amount of silane of Formula A may be more than one silane molecule per hydroxyl group of the polydimethylsiloxane. In the later case, the silane of Formula B can be added before the silane of Formula A completely reacts with the hydroxyl groups of the polydimethylsiloxane. After the silane of Formula A reacts with the hydroxyl of the polydimethylsiloxane, a silane having two hydrolyzable groups per molecule is added. These silanes preferably have a fast reaction time with the hydroxyl of the polydimethylsiloxane. The silanes with two hydrolyzable groups per molecule have a formula $R_2SiX_2$  Formula B in which R and X are defined above. Such silanes can be illustrated by methylvinylbis (N-methylacetamido) silane, dimethyldimethoxysilane, dimethyldiacetoxysilane, dimethylbis(ethylmethylketomixo)silane, and methylvinyldiethoxysilane. R can be a monovalent hydrocarbon radical and is illustrated by methyl, ethyl, propyl,-butyl, pentyl, phenyl, cyclohexyl, vinyl, allyl, hexenyl, and cyclohexenyl. Y can be a hydroxylable group and can be illustrated by alkoxy groups such as methoxy, ethoxy, n-propoxy, and butoxy; ketoximo groups such as ethylmethylketomixo and dimethylketoximo; carboxyate groups of the formula $$R'\overset{O}{\underset{\|}{C}}-O-$$

in which R' is an alkyl group of one to eight carbon atoms, such as methyl, ethyl, propyl, butyl, octyl; amido groups such as N-methylacetamido and N-methylbenzamido; and alkenyloxy such as vinyloxy. The amount of silane of Formula A and the amount of silane of Formula B used can be varied to obtain a desired modulus. Decreasing the amount of the silane of Formula A and increasing the amount of the silane of Formula B decreases the modulus of the resulting cured elastomeric polyorganosiloxane, i.e. the sealant. Some silanes readily react with the silicon-bonded hydroxyl group (siloxanol) of the polydimethylsiloxane at room temperature without a catalyst whereas others may require either heating, the presence of a catalyst for the reaction or both. Those silanes which readily react with the siloxanols without a catalyst are preferably used to make the polydimethylsiloxane (A) by this method.

A preferred method of making polydimethylsiloxanes of (A) is to mix hydroxyl endblocked polydimethylsiloxane with hydrolyzable silane (B) of the formula $R_{(4-c)}SiY_c$ in which c is 3 or 4, some Y are ketoximo groups and some Y are methoxy groups, and R is methyl radical, and thereafter add a hydrolyzable silane of the formula $R_2SiX_2$ in which X is N-methylacetamido, and R is methyl or vinyl radical. These mixtures can react merely by mixing at room temperature in an environment which protects them from contacting moisture and produce polydimethylsiloxanes of (A) in which the low reactivity endgroups have a formula $XR_2SiO-$ where X is methoxy or methylethylketoximo, and R is methyl or vinyl. The high reactivity endgroups have a formula

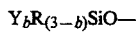
$$Y_b R_{(3-b)} SiO-$$

in which b is 2 or 3, R is methyl radical, and some Y are ketoximo groups and some Y are methoxy groups.

Polydimethylsiloxane of (A) can be those described by Kamis et al in U.S. Pat. No. 4,898,910, issued Feb. 6, 1990, which is hereby incorporated by reference to show polydimethylsiloxanes which have both vinyl endblocking and alkoxysilethylene endblocking. The polydimethylsiloxanes of Kamis et al are mixtures having the average formula

$$\begin{array}{c} \text{Me} \quad \text{Me} \quad \text{Me} \\ | \quad\quad | \quad\quad | \\ D-SiO(SiO)_y Si-D \\ | \quad\quad | \quad\quad | \\ \text{Me} \quad \text{Me} \quad \text{Me} \end{array}$$

in which Me is methyl radical, y has a value such that the viscosity is within the range of from 3 to 400 Pa.s, each D is a group selected from the group consisting of vinyl radical and radicals of the formula

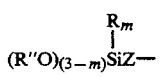
$$(R''O)_{(3-m)} \overset{R_m}{\underset{|}{Si}} Z-$$

which Z is a divalent hydrocarbon radical or combination of divalent hydrocarbon radicals and siloxane radicals, R" is methyl, ethyl, propyl, or butyl, m is 0 or 1, where >0% to ≦30% of the D groups are vinyl radicals.

The polydimethylsiloxanes of (A) described by Kamis et al can be produced by reacting in the presence of a platinum catalyst a vinyl endblocked polydimethylsiloxane of the formula

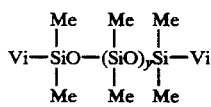
$$\begin{array}{c} \text{Me} \quad \text{Me} \quad \text{Me} \\ | \quad\quad | \quad\quad | \\ Vi-SiO-(SiO)_y Si-Vi \\ | \quad\quad | \quad\quad | \\ \text{Me} \quad \text{Me} \quad \text{Me} \end{array}$$

where Vi is a vinyl radical, and Me and x are defined above, with an endcapping compound of the formula

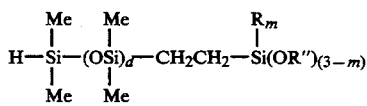
$$\begin{array}{c} \text{Me} \quad \text{Me} \quad\quad\quad R_m \\ | \quad\quad | \quad\quad\quad\quad | \\ H-Si-(OSi)_d-CH_2CH_2-Si(OR'')_{(3-m)} \\ | \quad\quad | \\ \text{Me} \quad \text{Me} \end{array}$$

in which R, R", and m are defined above, and d is 1 to 6. This endcapping compound can be made by reacting in the presence of a platinum catalyst one mole of a silane of the formula

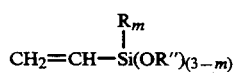
$$CH_2=CH-\overset{R_m}{\underset{|}{Si}}(OR'')_{(3-m)}$$

with at least two moles of silicon-bonded hydrogen atom endblocked polydimethylsiloxane of the formula

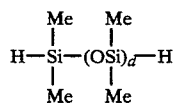
$$\begin{array}{c} \text{Me} \quad \text{Me} \\ | \quad\quad | \\ H-Si-(OSi)_d-H \\ | \quad\quad | \\ \text{Me} \quad \text{Me} \end{array}$$

where d is defined above. Any excess silicon-bonded hydrogen endblocked polydimethylsiloxane can be removed by a stripping process.

Another method of preparing polydimethylsiloxanes of (A) is reacting a hexaorganodisilazane with a hydroxyl endblocked polydimethylsiloxane where the amount of hexaorganodisilazane is sufficient to provide >0% to ≦30% low reactivity triorganosilyl end groups.

The hydrolyzable silanes of (B) have the formula

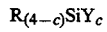
$$R_{(4-c)} SiY_c$$

in which R is a monovalent hydrocarbon radical, Y is a hydrolyzable group containing at least one carbon atom, and c has an average value of from 2 to 4. These hydrolyzable silanes preferably have 3 or 4 Y groups. Y can be ketoximo, alkoxy, acyloxy, alkenyloxy, and amido. Ketoximo can be —O—N=X where X is R"2= or

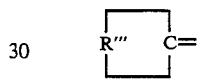
$$\begin{array}{c} \boxed{R''' \quad C=} \end{array}$$

in which R" is an alkyl of 1 to 5 carbon atoms, phenyl or vinyl, R''' is a divalent hydrocarbon radical. Examples of hydrolyzable silanes in which Y is a ketoximo include MeSi(O—N=CMeEt)3, ViSi(O—N=CMeEt)3, Si(O—N=CMeEt)4, and PhSi(O—N=CMeEt)3. These and other ketoximo silanes can be found in U.S. Pat. No. 3,184,427, issued May 18, 1965, to Russell et al; and U.S. Pat. No. 3,189,576, issued Jun. 15, 1965, to Sweet. Both Russell et al and Sweet are hereby incorporated by reference to show ketoximosilanes and there preparation. The ketoximosilanes are preferred because of their neutral properties, reactivity, and cured properties.

Y can be alkoxy as illustrated by methoxy, ethoxy, propoxy, isopropoxy, and methoxyethoxy. Examples of hydrolyzable silanes in which Y is alkoxy include methyltrimethoxysilane, vinyltrimethoxysilane, phenyltrimethoxysilane, vinyltriethoxysilane, tetraethyl orthosilicate, tetramethyl orthosilicate, ethyltrimethoxysilane, propyltrimethoxysilane, methyltriethoxysilane, phenyltriethoxysilane, butyltripropoxysilane, pentyltriisopropoxysilane, methyldimethoxyethoxysilane, and methyldiethoxymethoxysilane.

Y can be acyloxy as illustrated by acetoxy and octanoyloxy. Examples of hydrolyzable silanes in which Y is acyloxy include methyltriacetoxysilane, ethyltriacetoxysilane, vinyltriacetoxysilane, methyltrioctanoyloxysilane, propyltriacetoxysilane, phenyltriacetoxysilane, and ethyltrioctanoyloxysilane.

Y can be alkenoxy as illustrated by propenoxy, isopropenoxy, and butenoxy. Examples of hydrolyzable silanes in which Y is alkenoxy include methyltripropenoxysilane, ethyltripropenoxysilane, and vinyltripropenoxysilane.

Y can be amido as illustrated by N-methylacetamido, N-ethylpropionamido, N-ethylbenzamido, N- phenylacetamido, and N-propylpropionamido. Examples of hydrolyzable silanes in which Y is amido include methyltri(N-methylacetamido)silane and vinyltri(N-methylacetamido)silane. The amido silanes are shown by Toporcer et al in U.S. Pat. No. 3,776,933, issued Dec. 4, 1973, which is hereby incorporated by reference to show the amidosilanes and their preparation.

The hydrolyzable silanes of (B) can be those in which the Y groups are different in the same silane. For example, silanes (B) can be those in which some Y are ketoximo and some Y are alkoxy. Such silanes are described by Klosowski et al in U.S. Pat. No. 4,657,967, issued Apr. 14, 1987, and by Haugsby et al in U.S. Pat. No. 4,973,623, issued Nov. 27, 1990, which are hereby incorporated by reference to show silanes which contain both ethoxy-ketoximo silanes and methods of their preparation.

The amount of hydrolyzable silane of (B) is that amount necessary to crosslink the polydimethylsiloxane of (A) and to protect the elastomeric polydimethylsiloxane composition from the ingress of moisture when packaged in a container. This amount is preferably at least one molecule of silane (B) per siloxanol of (A). Such amounts are usually from 1 to 10 weight percent silane (B) based on the weight of the composition.

The siloxaphobic agent of (C) is one of the materials which provides the siloxaphobic surface layer of the cured elastomeric polyorganosiloxane composition. This siloxaphobic agent is a fluorocarbon alcohol, a reaction product of a fluorocarbon alcohol and a hydrolyzable silane of (B), or a mixture of the fluorocarbon alcohol and the reaction product of the fluorocarbon alcohol and the hydrolyzable silane. The fluorocarbon alcohol contains at least one fluorocarbon group of the formula $C_xF_{(2x+1)}$— group where x has an average value of at least 6. Fluorocarbon alcohols which have fluorocarbon groups where x was less than 6 did not prevent the migration of siloxane species to the surface of the sealant. Preferably, the fluorocarbon alcohols are those with fluorocarbon groups in which x has an average value of from 6 to 20. The fluorocarbon alcohols are commercially available and are illustrated by the following formulae

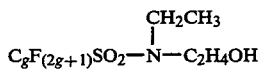

where g has a value of from 6 to 20. Commercial mixtures are sold in which g has an average of 7.5 and contain species in which g ranges from 4 to 10 inclusive. Such a mixture is FC-10 which is sold by Minnesota Mining and Manufacturing Company (3M), Minneapolis, Minn. Other commercial mixtures sold by 3M are FC-170C which is a fluorocarbon alcohol and has the following average formula

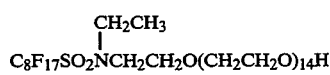

and FC-171 which is a fluorocarbon alcohol and has the following average formula

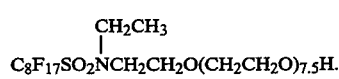

Other commercially available fluorocarbon alcohols include $C_8F_{17}CH_2CH_2OH$, and $C_xF_{(2x+1)}CH_2CH_2O(CH_2CH_2O)_fH$ where x is from 6 to 16 and f is a positive integer.

The siloxaphobic agent is preferably a reaction product of a fluorocarbon alcohol and a hydrolyzable silane. These siloxaphobic agents are siloxaphobic reaction product mixtures which are made by mixing at least 0.01 mole of the fluorocarbon alcohol with one mole of the hydrolyzable silane under conditions which exclude moisture from contacting the ingredients, preferably 0.1 mole of fluorocarbon alcohol per one mole of hydrolyzable silane. Fluorocarbon alcohols can be used by themselves but some are solid at room temperature and handling and mixing with the other ingredients is not fully acceptable. The fluorocarbon alcohols are described above and the hydrolyzable silanes are those of (B). The resulting mixture is heated until some of the fluorocarbon alcohol reacts with the hydrolyzable silane and forms a C—O—Si bond. The resulting reaction mixture is unreacted hydrolyzable silane, unreacted fluorocarbon alcohol, and a reaction product of fluorocarbon alcohol and the hydrolyzable silane (B) in which at least one Y group is replaced by the fluorocarbon alcohol, as illustrated by the following equation

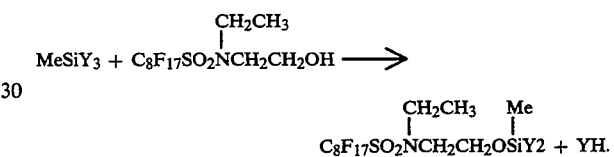

The siloxaphobic reaction product mixtures contain from >0% to 100% reaction product of fluorocarbon alcohol and silane (B). These reaction product mixtures provide the preferred siloxaphobic agents, especially when the reaction product of the fluorocarbon alcohol and silane (B) is <50% of the siloxaphobic reaction mixture.

A preferred siloxaphobic reaction mixture is one in which the fluorocarbon alcohol has the following formula

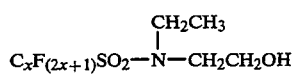

wherein x has an average value of at least 6, the hydrolyzable silane has the formula

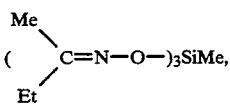

and the reaction product of the fluorocarbon alcohol and the hydrolyzable silane comprises a compound of the formula

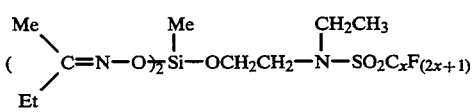

wherein x has an average value of at least 6.

The siloxaphobic reaction mixture is preferred because the siloxaphobic surface layer is rapidly formed during the curing of the elastomeric polyorganosiloxane composition and the surface resists the accumulation of dirt and/or stain when the sealant is very vulnerable to dirt pick-up. The siloxaphobic reaction mixture through some unknown mechanism more readily forms the siloxaphobic surface layer than the use of unreacted fluorocarbon alcohol, i.e. the fluorocarbon alcohol is merely mixed with the other elastomeric polydimethylsiloxane composition ingredients. The siloxaphobic surface layer is regenerated over the useful life of the sealant. The siloxaphobic reaction mixture acts as a reservoir and continually renews the siloxaphobic surface layer as it becomes depleted with age. The siloxaphobic surface layer also provides a sealant which exhibits retardation of color formation of the sealant surface and the surrounding areas adjacent to the sealant which may be the result of exposure to weather. The siloxaphobic surface layer keeps the properties of the sealant from changing with age because siloxane ingredients are not readily lost by migration or evaporation, but are maintained within the sealant matrix. The siloxaphobic reaction mixture does not adversely effect the curing properties of the elastomeric polydimethylsiloxane composition, and the adhesion to various substrates, particularly those used in building construction, does not appear to be altered by addition of the siloxaphobic reaction mixture to the composition. The siloxaphobic reaction mixture can be used in small amounts and yet provide its useful properties over long periods of time. The amounts are such that the fluorocarbon group is present in the composition in amounts of from 0.1 to 7 inclusive weight percent based on the weight of the composition, preferably from 1 to 3 weight percent.

The polydimethylsiloxane compositions which cures to elastomers can also contain a filler. These fillers can be those generally used in formulating silicone sealants, and include both reinforcing fillers such as fumed silica, hydrophobicized fumed silica, hydrophobicized precipitated silica, and carbon black and non-reinforcing fillers such as calcium carbonate, stearic acid treated calcium carbonate, precipitated calcium carbonate, finely pulverized quartz, diatomaceous earth, titanium dioxide, alumina, iron oxide, magnesium oxide, and zinc oxide. The calcium carbonate fillers are preferred because they appear to act as a reservoir for the fluorocarbon alcohol, which extend the useful life of the siloxaphobic agent.

The polydimethylsiloxane compositions which cure to elastomers and which contain ingredients (A) through (D) have enhanced siloxaphobic properties by the addition of at least 0.5 weight percent of a drying oil based on the weight of the composition. These drying oils are described above and increase the siloxaphobic characteristics of the cured sealant. They also provide a surface which is paintable with both oil based paints and latex paints wherein paints are materials used to enhance the aesthetics of a substrate as well as protect it from the environment and are pigmented to various colors. The drying oil which is preferred is tung oil. When a drying oil, such as tung oil, is used it may be added just before use or it may be mixed with the other ingredients into what is known as a one package sealant. In the latter case, it is required that the package be an airless package because drying oils react with atmospheric oxygen and therefore, compositions which contain a drying oil need to be protected from air until it is desirable to cure them. Some drying oils may require the use of accelerators to achieve their properties. Accelerators can be used as long as they do not interfere with the other properties of the sealant, its storage, its cure, or its manufacture. These accelerators are known in the paint art as driers. Also, the use of photoinitiators with the drying oils may be useful in these compositions.

The polydimethylsiloxane compositions which cure to elastomers may find a catalyst for curing useful to develop the sealant properties within an acceptable period of time. With some hydrolyzable silanes of (B) catalysts are generally required. For example, alkoxysilanes require a catalyst for cure in satisfactory time periods and such catalyst can include tin catalysts such as dibutyltin dicarboxylates such as dibuthyltin dilaurate, dibutyltin diacetate, dibutyltin dioctoate, stannous octoate, and stannous 2-ethylhexoate; and titanium catalyst such as tetrabutyltitanate, tetraisopropyltitanate, bis-(acetylacetonyl)diisopropyltitanate, and 2,5-diisopropoxy-bis-ethylacetoacetate titanium. These catalysts are well known in the art of silicone sealants. Compositions which are made by using ketoximosilanes for ingredient (B) preferably contain a mixture of tin catalyst and titanium catalyst. The preferred catalysts are dibutyltin dilaurate and 2,5-diisopropoxy-bis-ethylacetoacetate titanium. The preferred amounts are from 0.05 to 0.2 part by weight of the tin catalyst based on 100 parts by weight of polydimethylsiloxane (A) and 0.1 to 2 parts by weight of the titanium catalyst based on 100 parts by weight of polydimethylsiloxane (A).

The polydimethylsiloxane compositions which cure to elastomers preferably contain a silane adhesion promoter. The breadth of substrates to which the sealants can be adhered can be increased as well as the consistency of the adhesion can be maintained by the addition of a silane adhesion promoter. The silanes which act as adhesion promoters are preferably aminoorganotrialkoxysilanes and glycidoxyorganotrialkoxysilane. Aminoorganotrialkoxysilanes are illustrated by gamma-aminopropyltriethoxysilane and N-beta-aminoethyl-gamma-aminopropyltrimethoxysilane. Glycidoxyorganotrialkoxysilanes are illustrated by gamma-(glycidoxy)propyltrimethoxysilane. In addition to providing adhesion to substrates, these silanes also increase the cure rate of the sealant, especially elastomeric polydimethylsiloxane compositions which contain as ingredient (B) ketoximosilanes. The amounts of such silane adhesion promoters is small, usually less than one weight percent of the composition, preferably less than 0.5 weight percent. The preferred silane adhesion promoters are mixtures of aminooorganotrialkoxysilane and glycidoxyorganotrialkoxysilane.

The preferred polydimethylsiloxane compositions of this invention which cure to elastomers contain a non-reinforcing thixotropic agent which can be illustrated by a polymer of 2,5-furandione with 1,3-butadiene. These non-reinforcing thixotropic agents increase the oleophobic character of the sealant and enhances the siloxaphobic surface layer properties of the sealant. Thixotropy is best enhanced when the non-reinforcing thixotropic agents are used with compositions containing calcium carbonate.

The following examples are for illustrative purposes and should not be construed as limiting the invention which is properly delineated in the claims. In the following examples, viscosities are at 25° C. "part" or "parts" are by weight, Me represent methyl radical, Vi represents vinyl radical.

EXAMPLE 1

A siloxaphobic reaction mixture was prepared by mixing in a closed vessel, 29 parts of a fluorocarbon alcohol, FC-10 manufactured by 3M, which has the average formula $$C_gF_{(2g+1)}SO_2-\underset{\underset{H}{|}}{N}-C_2H_4OH$$

where g has an average value of 7.5 and contains species having g values of 4, 5, 6, 7, and 8, and 71 parts of a ketoximosilane mixture which was approximately 70 weight percent methyltri(methylethylketoximo)silane, 24 weight percent methyldi(methylethylketoximo)methoxysilane, 0.5 weight percent methyldimethoxy(methylethylketoximo)silane, and 5.5 weight percent impurities. The resulting mixture was heated at 50° C. for 30 minutes under a nitrogen purge. The resulting siloxaphobic reaction mixture was 19.7 weight percent unreacted fluorocarbon alcohol, 59.9 weight percent unreacted ketoximosilane, and 12.3 weight percent reaction product of the formula $$(\underset{Et}{\overset{Me}{\diagdown}}C=N-O-)_2Si-OCH_2CH_2-\underset{\underset{H}{|}}{N}-SO_2C_gF_{(2g+1)}$$

and 8.1 weight percent impurities. This siloxaphobic reaction mixture was used as obtained and for these examples is designated Siloxaphobic Agent A.

Siloxaphobic Agent B was made in the same manner as Siloxaphobic Agent A, except 33 parts of FC-10 and 67 parts of the ketoximosilane mixture were used and a nitrogen purge was not used.

Siloxaphobic Agent C was made in the same manner as Siloxaphobic Agent A, except 23 parts of FC-10 and 77 parts of the ketoximosilane mixture were used and a nitrogen puree was not used.

Siloxaphobic Agent D was made in the same manner as Siloxaphobic Agent A, except 45.5 parts of FC-10 and 54.5 parts of the ketoximosilane mixture were used and a nitrogen purge was not used.

EXAMPLE 2

Polydimethylsiloxane compositions which were cured to elastomers were prepared by using the following ingredients Polymer A = a hydroxyl endblocked polydimethylsiloxane having a viscosity of 50 Pa.s
Polymer B = a hydroxyl endblocked polydimethylsiloxane having a viscosity of 200 Pa.s
Polymer C = a hydroxyl endblocked polydimethylsiloxane having a viscosity of 4 Pa.s
Silane A = a ketoximosilane mixture of approximately 70 weight percent methyltri(methylethylketoximo)silane, 24 weight percent methyldi(methylethylketoximo)methoxysilane, 0.5 weight percent methyldimethoxy(methylethylketoximo)silane, and 5.5 weight percent impurities
Silane B = methylvinyldi(N-methylacetamido)silane
Filler A = stearic acid treated precipitated calcium carbonate
Filler B = stearic acid treated ground calcium carbonate
Thixotropic Agent = a polymer of 2,5-furandione with 1,3-butadiene
Adhesion Promoter A = gamma-aminopropyltriethoxysilane
Adhesion Promoter B = gamma-(glycidoxy)propyltrimethoxysilane
Adhesion Promoter C = N-beta-aminoethyl-gamma-aminopropyltrimethoxysilane
Catalyst A = dibutyltin dilaurate
Catalyst B = diisopropoxy-bis-(ethylacetoacetate) titanium Polydimethylsiloxane compositions which cured to elastomers of Formulations 1–8 were prepared by mixing Polymer A, Polymer B, and Polymer C with Silane A in the amounts as shown in Table I, which also shows the amounts of the other ingredients used to make the compositions. To the resulting mixture, Siloxaphobic Agent B, C, or D as described in Example 1, Filler A, Filler B, Thixotropic Agent, Adhesion Promoter A, Adhesion Promoter B, Catalyst A, and Catalyst B were in the amounts as shown in Table 1.

The polydimethylsiloxane compositions which cured to elastomers of Formulations 9–14 were prepared by mixing Polymer A, Polymer B, and Polymer C with Silane A in the amounts shown in Table 2. After the polymer was mixed with Silane A, Silane B was added to provide a polydimethylsiloxane which had both low reactivity endgroups of the formula $$X-\underset{\underset{Vi}{|}}{\overset{\overset{Me}{|}}{Si}}-O-$$

where X is either methoxy or methylethylketoximo, and high reactivity endgroups of the formula Y$_2$MeSiO— in which some Y are methylethylketoximo groups and some Y are methoxy groups. The reaction of Silane B with the unreacted hydroxyl groups of 0 Polymer A, Polymer B, and Polymer C was very fast and was essentially complete after mixing. The remaining ingredients and their amounts were as shown in Table 2.

The resulting polydimethylsiloxane compositions (sealant composition) of Formulations 1–14 were prepared under conditions which protected against the ingress of moisture and were stored in packages which protected them from moisture. The staining and dirt pick-up property was evaluated by placing a horizontal bead of about 1.9 cm width and 0.6 cm depth across the top of a panel having a polished ceramic surface with mortar backing (Glassweld panel). The panels were then set outside at a 45 degree angle facing south for four months. After the outside exposure of four months and six months, the panels were evaluated for sealant surface dirt pick-up and staining was evaluated after four months and and given the following rating: 1 = as clean as a panel without a sealant bead; 2 = no streaks, panel and sealant are mainly clean, but not as clean as a panel without a sealant bead; 3 = slight streaks, panel looks slightly hazy from staining, very little dirt pick-up on sealant which cannot be seen from more than 1.5 meters away; 4 = moderate streaks, panel is hazy overall, some dirt pick-up on sealant that is visible at 1.5 meters away; and 5 = heavy/dark streaks, panel has heavy film covering it, and the sealant has turned dark from dirt. The results of the stain and dirt pick-up test were as shown in Table 3. The 100% elongation modulus was measured after allowing the sealant to cure for seven days at room temperature. The modulus was determined by ASTM D-412 and the results are shown in kPa. The percent extractables, after curing for seven days at room temperature, was determined in accordance with ASTM D-3971-69 procedure using toluene as the solvent, a time period of 24 hours, and the cured sealant pieces were 3.175 mm by 3.175 mm by 2.54 mm. The contact angle using trimethylsilyl endblocked polydimethylsiloxane having a viscosity of 0.1 Pa.s was determined and the results were as shown in Table 3. The contact angle determination was done in the same manner as would be used for determining the contact angle of water, except that trimethylsilyl endblocked polydimethylsiloxane was used in place of the water. The surface energy was determined by water contact angle and methylene iodide contact angle for obtaining the dispersive force component and the polar force component using the equation of Owen et al in the Journal of Applied Polymer Science, 1969, vol. 13, beginning at page 1741.

TABLE 1

| Ingredients | Formulation, In Parts | | | | | | | |
|---|---|---|---|---|---|---|---|---|
| | 1 | 2 | 3 | 4 | 5 | 6 | 7 | 8 |
| Polymer A | 100 | 100 | 100 | 100 | 0 | 0 | 0 | 0 |
| Polymer B | 0 | 0 | 0 | 0 | 100 | 100 | 100 | 100 |
| Polymer C | 0 | 0 | 20 | 20 | 20 | 20 | 0 | 0 |
| Silane A | 0.5 | 0.5 | 2.5 | 2.5 | 0.5 | 0.5 | 2.5 | 2.5 |
| Silane B | 0 | 0 | 0 | 0 | 0 | 0 | 0 | 0 |
| Siloxapholic Agent B | 9 | 9 | 0 | 0 | 15 | 15 | 0 | 0 |
| Siloxapholic Agent C | 0 | 0 | 0 | 0 | 0 | 0 | 13 | 13 |
| Siloxapholic Agent D | 0 | 0 | 11 | 11 | 0 | 0 | 0 | 0 |
| Filler A | 35 | 35 | 60 | 60 | 35 | 35 | 60 | 60 |
| Filler B | 0 | 50 | 50 | 0 | 0 | 50 | 50 | 0 |
| Thixotropic Agent | 0.5 | 3 | 3 | 0.5 | 3 | 0.5 | 0.5 | 3 |
| Adhesion Promoter A | 0.25 | 0.9 | 0.25 | 0.9 | 0.9 | 0.25 | 0.9 | 0.25 |
| Adhesion Promoter B | 0.1 | 2 | 0.1 | 2 | 0.1 | 2 | 0.1 | 2 |
| Catalyst A | 0.07 | 0.15 | 0.15 | 0.07 | 0.15 | 0.07 | 0.07 | 0.15 |
| Catalyst B | 0 | 1 | 0 | 1 | 1 | 0 | 1 | 0 |

TABLE 2

| Ingredients | Formulation, In Parts | | | | | |
|---|---|---|---|---|---|---|
| | 9 | 10 | 11 | 12 | 13 | 14 |
| Polymers A | 100 | 100 | 100 | 0 | 0 | 0 |
| Polymers B | 0 | 0 | 0 | 100 | 100 | 100 |
| Polymer C | 0 | 20 | 20 | 20 | 0 | 0 |
| Silane A | 0.5 | 2.5 | 2.5 | 0.5 | 2.5 | 2.5 |
| Silane B | 2 | 2 | 2 | 2 | 2 | 2 |
| Siloxapholic Agent B | 15 | 0 | 0 | 9 | 0 | 0 |
| Siloxapholic Agent C | 0 | 13 | 13 | 0 | 0 | 0 |
| Siloxapholic Agent D | 0 | 0 | 0 | 0 | 11 | 11 |
| Filler A | 60 | 35 | 35 | 60 | 35 | 35 |
| Filler B | 0 | 0 | 50 | 50 | 0 | 50 |
| Thixotropic Agent | 0.5 | 0.5 | 3 | 0.5 | 3 | 0.5 |
| Adhesion Promoter A | 0.25 | 0.9 | 0.25 | 0.25 | 0.25 | 0.9 |
| Adhesion Promoter B | 0.1 | 2 | 0.1 | 2 | 2 | 0.1 |
| Catalyst A | 0.15 | 0.15 | 0.07 | 0.15 | 0.07 | 0.15 |
| Catalyst B | 1 | 0 | 1 | 1 | 1 | 0 |

TABLE 3

| Example | Sealant Surface Dirt Pick-up After | | Stain After 4 & 6 Months | 100% Modulus (kPa) | Extractable (Wt. %) | Surface Energy Data | | 200 Fluid Contact Angle |
|---|---|---|---|---|---|---|---|---|
| | 4 Months | 6 Months | | | | Dispersive Force dynes/cm$^2$ | Polar Force dynes/cm$^2$ | |
| 1 | 1 | 1 | 1 | 483 | 4.9 | 13.6 | 11.1 | 31 |
| 2 | 1 | 1 | 1 | 517 | 4.4 | 11.3 | 16.8 | 37 |
| 3 | 2 | 1-2 | 1 | 552 | 4.1 | 14.6 | 1.2 | 52 |
| 4 | 2 | 2 | 1 | 538 | 6.7 | 15.7 | 9.6 | 21 |
| 5 | 1 | 1 | 1 | 662 | 3.6 | 10.2 | 19.8 | 31 |
| 6 | 3 | 1-2 | 1 | 331 | 5.8 | 15.7 | 12.9 | 21 |
| 7 | 3 | 2 | 1 | 565 | 3.3 | 20.8 | 0.4 | 16 |
| 8 | 1 | 1 | 1 | 772 | 4.8 | 10.3 | 15.4 | 39 |
| 9 | 2 | 3-4 | 1 | 200 | 13.8 | 11.2 | 20.2 | 35 |
| 10 | 3 | 1-2 | 1 | 400 | 7.8 | 11.1 | 13.7 | 49 |
| 11 | 3 | 2 | 1 | 338 | 5.1 | 7.13 | 14.5 | 59 |
| 12 | 3 | 3 | 1 | 117 | 23.6 | 6.9 | 17.9 | 62 |
| 13 | 2 | 2 | 1 | 303 | 10.2 | 5.9 | 27.9 | 60 |
| 14 | 1 | 1 | 1 | 365 | 5.1 | 11.9 | 23.3 | 35 |

EXAMPLE 3

Polydimethylsiloxane compositions which cured to elastomers of Formulations 17, 18, and 19 were prepared as described in Example 2 for Formulations 9-14 using the ingredients as identified in Table 4. Instead of using FC-10, the Siloxaphobic Agent A of Example 1 was used with the amounts shown in Table 4. In Formulations 18 and 19, titanium dioxide pigment was used, and in Formulation 19, tung oil was used. For Formulations 18 and 19, Polymer A by reaction with Silane A and Silane B resulted in a polydimethylsiloxane with low reactivity endgroups and high reactivity endgroups as described in Example 2 for Formulations 9-14. The results of staining and dirt pick-up, 100% modulus after curing at room temperature for 7 days, and the contact angle as described in Example 2 were determined and were as shown in Table 4, except the panels used for exposure to outside atmospheric conditions were reflective glass panels and the sealant beads were applied in a square root shape of 5 cm width and 0.6 cm depth across the top of the panel. The panels were placed in an industrial environment.

TABLE 4

| Ingredients | Formulation, In Parts | | |
|---|---|---|---|
| | 17 | 18 | 19 |
| Polymer A | 100 | 100 | 100 |
| Silane A | 2 | 1 | 1 |
| Silane B | 2 | 1 | 1 |
| Siloxaphobic Agent A | 9 | 10 | 10 |
| Filler A | 40 | 60 | 60 |
| Filler B | 50 | 0 | 0 |
| Thixotropic Agent | 0.5 | 0.5 | 0.5 |
| Adhesion Promoter A | 0.3 | 0 | 0 |
| Adhesion Promoter B | 0.7 | 0.1 | 0.1 |
| Adhesion Promoter C | 0 | 0.3 | 0.3 |
| Catalyst A | 0.16 | 0.07 | 0.07 |
| Catalyst B | 0.5 | 1 | 1 |
| TiO$_2$ Pigment | 0 | 9 | 9 |
| Tung Oil | 0 | 1 | 0 |
| Staining and Dirt Pick-up After: | | | |
| 3 Months | 1–2 | 1 | 1–2 |
| 6 Months | 2 | — | — |
| 100% Modulus (kPa) | 165 | 228 | 255 |
| 200 Fluid Contact Angle* | 28 | 37 | 31 |
| Dispersive Force, dynes/cm$^2$ | 12.6 | 9.9 | 14.3 |
| Polar Force, dynes/cm$^2$ | 15.3 | 12.7 | 5.9 |

*Measured After Outdoor Exposure

Formulation 17 was cured for 7 days at room temperature and also cured for 7 weeks at 50° C. The tensile strength at break, the elongation at break, and the 100% modulus were measured by ASTM D-412. The durometer on the Shore A scale was measured in accordance with ASTM C-661 procedure. The percent extractables was determined in accordance with ASTM D-3971-69 procedure using toluene as the solvent, a time period of 24 hours, and the cured sealant pieces were 3.175 mm by 3.175 mm by 2.54 mm. The results observed were as follows:

TABLE 5

| | After Room Temperature Cure | After Cure at 50° C. |
|---|---|---|
| Tensile Strength at break, kPa | 1379 | 1255 |
| Elongation at break, % | 915 | 522 |
| 100% Modulus, kPa | 165 | 365 |
| Durometer, Shore A | 14 | 28 |
| Extractables, % | 6.7 | — |

The contact angle and the surface energies were measured after 3 months exposure and after 6 months exposure. The contact angle as determined in Example 2 was 28 degrees after both exposures. The dispersive force component of the surface energy was 13.1 dynes/cm$^2$ after 3 months exposure and 12.6 dynes/cm$^2$ after 6 months exposure. These low dispersive force components showed that the sealant surface repulsed both siloxane fluid and soot, and that free siloxane materials were not able to migrate out of the sealant onto the sealant surface. The polar force component of the surface energy was 18.5 dynes/cm$^2$ after 3 months exposure and 14.7 dynes/cm$^2$ after 6 months exposure. The total surface energies were 31.5 dynes/cm$^2$ after 3 months exposure and 27.3 dynes/cm$^2$ after 6 months exposure.

EXAMPLE 4

Polydimethylsiloxane compositions which cured to elastomers of Formulations 20–23 were prepared by mixing 85 parts of a polydimethylsiloxane having a viscosity of 16.5 Pa.s and having 85% of the endgroups being hydroxyl and 15% of the endgroups being trimethylsilyl groups where this polydimethylsiloxane was prepared in the manner described by Dupree, 10.5 parts of fumed silica filler, 2.24 parts of methyltriacetoxysilane, 2.24 parts of ethyltriacetoxysilane, and 0.02 part of dibutyltin diacetate. To portions of this elastomeric polydimethylsiloxane composition, the following amounts of FC-10 (as described in Example 1) was added: Formulation 20, 1 weight percent; Formulation 21, 3 weight percent, Formulation 22, 6.5 weight percent, and Formulation 23, none. The staining and dirt pick-up was evaluated by making test panels as described in Example 3 and evaluating them after exposures of 4 months, 8 months, and 11 months. The results were as shown in Table 6. The results showed that the fluorocarbon alcohol did improve the sealant surface dirt pick-up, but the staining was only marginally improved.

TABLE 6

| | Staining After | | | Dirt Pick-up After | | |
|---|---|---|---|---|---|---|
| Formulation | 4 Months | 8 Months | 11 Months | 4 Months | 8 Months | 11 Months |
| 20 | 2 | 3–4 | 4 | 1 | 3 | 3 |
| 21 | 2–3 | 3 | 3 | 1 | 1 | 1 |
| 22 | 2–3 | 3 | 3 | 1 | 1 | 1 |
| 23 | 2 | 3–4 | 4 | 3 | 4 | 4 |

EXAMPLE 5

A polydimethylsiloxane composition which cured to elastomer was prepared as described in Example 2, except the ingredients and their amounts were: 100 parts of Polymer A, 1 part of Silane A, 1 part of Silane B, 10 parts of Siloxaphobic Agent A, 60 parts of Filler A, 0.5 part of Thixotropic Agent, 0.3 part of Adhesion Promoter A, 0.1 part of Adhesion Promoter B, 0.07 part of Catalyst A, and 1 part of Catalyst B.

The resulting composition had an extrusion rate of 139 g/min and upon exposure had a skin over time of 170 minutes. The composition was allowed to cure for 7 days at room temperature exposed to the atmosphere, test pieces were made, and using ASTM D-412, the tensile strength at break was 1538 kPa, the elongation at break was 931%, the 100% modulus was 159 kPa, and the tear strength (Die B) was 5.6 kN/m (kilonewtons/meter). The durometer on the Shore A scale as determined by ASTM C-661 was 12 and the amount of extractables as determined in Example 2 was 6%. After allowing the composition to cure for 7 days at room temperature and then for one month at 50° C., the properties were: tensile strength at break=2089 kPa, elongation at break=788%, 100% modulus=324 kPa, durometer on the Shore A scale =25, the tear strength (Die B)=5 kN/m, and the amount of extractable=8%.

Tung oil in the amount of one weight percent based on the weight of the composition was added to the above composition and thoroughly mixed. The resulting composition was allowed to cure at room temperature for two weeks after which a portion of the cured surface was painted with a deep blue latex paint and another portion was painted with a red oil based paint.

After two days the oil based paint adhered to the cured sealant surface. The latex paint took 17 days to develop partial adhesion to the cured sealant surface and fully adhered after 43 days. The surface of cured sealant without the tung oil would not wet with latex paint and although the oil based paint spread evenly over the surface of the sealant without the tung oil, it did not adhere.

EXAMPLE 6

Siloxaphobic agents were prepared by mixing, under a dry nitrogen purge, FC-10 as defined in Example 1 and Silane A in the amounts as shown in Table 7, and then heating at 70° C. for 2.75 hours. The resulting mixtures were analyzed by gas chromatography and the results observed were as shown in Table 7 in weight ratios.

TABLE 7

| SILOXA-PHOBIC AGENT MIXTURE | FC-10 moles | Moles of ketoximo in Silane A | MEKO[1] | SILANE I[2] | SILANE II[3] |
|---|---|---|---|---|---|
| 1 | 0 | 3 | 2.8 | 16.2 | 58.0 |
| 2 | 1 | 3 | 14.5 | 13.2 | 19.9 |
| 3 | 2 | 3 | 19.0 | 7.7 | 10.2 |
| 4 | 3 | 3 | 24.5 | 3.8 | 2.2 |
| 5 | 3 | 2 | 29.2 | 0.4 | 0.0 |

| SILOXA-PHOBIC AGENT MIXTURE | REACTION PRODUCT[4] | REACTION PRODUCT[5] | REACTION PRODUCT[6] |
|---|---|---|---|
| 1 | 0.0 | 0.0 | 0.0 |
| 2 | 1.0 | 13.2 | 0.0 |
| 3 | 2.2 | 23.6 | 2.8 |
| 4 | 4.4 | 22.3 | 8.9 |
| 5 | 4.2 | 8.4 | 17.3 |

[1]MEKO = methylethylketoxime
[2]methylmonomethoxydi(methylethylketoximo)silane
[3]methyltri(methylethylketoximo)silane
[4]dimer of methyltri(methylethylketoximo)silane
[5]a reaction product of FC-10 and methyltri(methylethylketoximo)silane of the formula

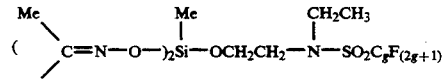

where g is defined in Example 1.
[6]a reaction product of FC-10 and methyltri(methylethylketoximo)silane of the formula

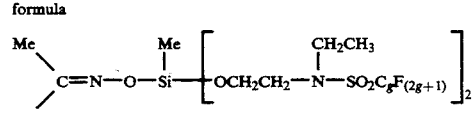

where g is defined in Example 1.

EXAMPLE 7

Siloxaphobic agents were prepared as described in Example 1 using FC-10 and Silane A except Siloxaphobic Agent E was heated for one hour at 70° C., Siloxaphobic Agent F was heated for 45 minutes at 50° C., and Siloxaphobic Agent G was made using a catalyst and was heated for 45 minutes at 50° C. These siloxaphobic agents were mixed into an elastomeric polydimethylsiloxane composition with the amounts of the ingredients shown by Table 8. These ingredients were mixed while being protected against the ingress of moisture into the composition. These compositions were used as a model study to observe differences in siloxaphobic agent preparation and to compare them with unreacted FC-10 and compositions without any fluorocarbon additive. The compositions were cured by exposure to air at room temperature for 7 days prior to observing the properties. The contact angle was measured as described in Example 2 and the dispersive force component of the surface energy was determined and the results observed were as shown in Table 8.

TABLE 8

| | FORMULATION, in parts | | | | |
|---|---|---|---|---|---|
| | 1 | 2 | 3 | 4 | 5 |
| Polymer A | 100 | 100 | 100 | 100 | 100 |
| Siloxaphobic Agent E | 13 | 0 | 0 | 0 | 0 |
| Siloxaphobic Agent F | 0 | 13 | 0 | 0 | 0 |
| Siloxaphobic Agent G | 0 | 0 | 15 | 0 | 0 |
| Silane A | 0 | 0 | 0 | 10 | 10 |
| FC-10 | 0 | 0 | 0 | 3 | 0 |
| Catalyst B | 1 | 1 | 0 | 1 | 1 |
| Adhesion Promoter A | 0.22 | 0.22 | 0 | 0.22 | 0.22 |
| Adhesion Promoter B | 0.48 | 0.48 | 0 | 0.48 | 0.48 |
| gamma-mercaptopropyl-trimethoxysilane | 0.3 | 0.3 | 0 | 0.3 | 0.3 |
| Contact Angle | 27 | 28 | 38 | 19 | 19 |
| Dispersive Force, dynes/cm$^2$ | 13.3 | 14.8 | 8.6 | 20.9 | 23.5 |

These results illustrate the significant reduction in dispersive force using the siloxaphobic agents of this invention.

EXAMPLE 8

A polydimethylsiloxane composition which cured to elastomer was prepared by mixing 100 parts of Polymer A, 5.2 parts of Silane A, 29 parts of Filler A, 69 parts of Filler B, a mixture (made from 5 parts of FC-10, 1 part of Catalyst B, 0.13 part of Adhesion Promoter A, 0.29 part of Adhesion Promoter B, and 0.32 part of gamma-mercaptopropyltrimethoxysilane) which was mixed and then let stand overnight before it was used, and 0.53 part of the thixotropic agent as described in Example 2. The resulting composition for this example is designated Sealant 1. To Sealant 1, 1 part of tung oil was added and this composition is designated Sealant 2 for this example. Each of these compositions were evaluated in an outside environment by making Glassweld test panels with a horizontal bead as described in Example 2. Using the rating described for dirt pick-up and staining described in Example 2, the results were as follows:

Sealant 1: dirt pick-up after 9 months=2, dirt pick-up after 13 months=2.5, staining after 9 months=1, staining after 11 months=1

Sealant 2: dirt pick-up after 9 months=1, dirt pick-up after 13 months=1 staining after 9 months=1, staining after 11 months=1

These results showed that a combination of fluorocarbon alcohol and tung oil oxidation product provided an increased siloxaphobic surface.

That which is claimed is:

1. A method comprising, under conditions to exclude moisture from contacting ingredients,
   (1) mixing a fluorocarbon alcohol containing per molecule at least one fluorocarbon group of the formula $C_xF_{(2x+1)}$— in which x has an average value of at least 6 and a hydrolyzable silane of the average general formula $R_{(4-c)}SiY_c$ wherein R is a monovalent hydrocarbon radical, c has an average value of from 2 to 4 inclusive and Y is a hydrolyzable group selected from the group consisting of ketoximo, alkoxy, acyloxy, alkenyloxy, and amido, make a mixture where there is at least 0.01 mole of fluorocarbon alcohol per one mole of hydrolyzable silane molecule, 92) heating the mixture of (1) until some of the fluorocarbon alcohol reacts with the hydrolyzable silane wherein a C—O—Si bond is formed and a reaction mixture of the hydrolyzable silane and the fluorocarbon alcohol results and comprises, unreacted fluorocarbon alcohol, unreacted hydrolyzable silane and a reaction product of the hydrolyzable silane and the fluorocarbon alcohol, and (3) mixing the produce of (2) with a room temperature curing elastomeric polyorganosiloxane composition in an amount such that there is from 0.1 to 7 weight percent of the fluorocarbon group based on the total weight of the composition to make a room temperature curing sealant which produces a siloxaphobic surface when cured by exposure to atmospheric conditions.

2. The method in accordance with claim 1 further comprising in (3) mixing a drying oil with the product of (2) and the room temperature curing elastomeric polyorganosiloxane composition where the drying oil is in an amount of from 0.5 to 5 weight percent based on the total weight of the composition.

3. The method in accordance with claim 1 further comprising packaging the room temperature curing sealant obtained in claim 37 in a container which substantially excludes atmospheric moisture from contacting the sealant.

4. The method in accordance with claim 3 further comprising in (3) mixing a drying oil with the product of (2) and the room temperature curing elastomeric polyorganosiloxane composition where the drying oil is in an amount of from 0.5 to 5 weight percent based on the total weight of the composition.

5. The method in accordance with claim 3 further comprising extruding the room temperature curing sealant from the container onto a substrate where a surface of the room temperature curing sealant is exposed to air and the surface at the interface with air forms a siloxaphobic surface layer when the sealant cures.

6. The method in accordance with claim 5 further comprising in (3) mixing a drying oil with the product of (2) and the room temperature curing elastomeric polyorganosiloxane sealant where the drying oil is in an amount of from 0.5 to 5 weight percent based on the total weight of the sealant.

7. The method in accordance with claim 2 in which the product of (2) is a mixture of a fluorocarbon alcohol of the following formula

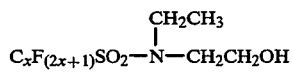

wherein x has an average value of at least 6, and a hydrolyzable silane reaction product comprising a compound of the formula

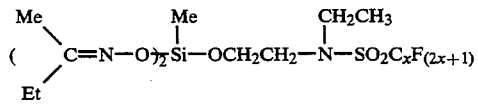

wherein x has an average value of at least 6 and the drying oil is tung oil.

8. The method in accordance with claim 4 in which the product of (2) is a mixture of a fluorocarbon alcohol of the following formula

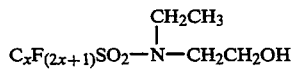

wherein x has an average value of at least 6, and a hydrolyzable silane reaction product comprising a compound of the formula

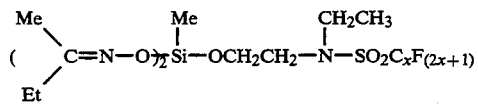

wherein x has an average value of at least 6 and the drying oil is tung oil.

9. The method in accordance with claim 6 in which the product of (2) is a mixture of a fluorocarbon alcohol of the following formula

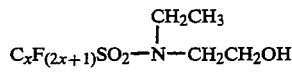

wherein X has an average value of at least 6, and a hydrolyzable silane reaction product comprising a compound of the formula

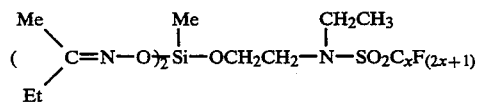

wherein x has an average value of at least 6 and the drying oil is tung oil.

10. A sealant obtained by exposing the product of claim 1 to atmospheric conditions.

11. A product obtained from the method of claim 3,

12. A sealant obtained by exposing the product of claim 4 to atmospheric conditions.

13. A product obtained from the method of claim 5.

14. A product obtained from the method of claim 6.

15. A sealant obtained by exposing the product of claim 7 to atmospheric conditions.

* * * * *